United States Patent [19]

Antonissen et al.

[11] Patent Number: 5,267,168
[45] Date of Patent: Nov. 30, 1993

[54] APPARATUS FOR AND METHOD OF CONTROLLING SLICING MACHINE

[75] Inventors: Peter Antonissen; Hugh M. Arthur, both of Norwich, England

[73] Assignee: Thurne Engineering Ltd., England

[21] Appl. No.: 676,012

[22] Filed: Mar. 27, 1991

[30] Foreign Application Priority Data

Mar. 27, 1990 [GB] United Kingdom ............. 9006804

[51] Int. Cl.$^5$ .................. G06F 15/46; B26D 5/20
[52] U.S. Cl. .................... 364/468; 83/75.5;
83/76.8; 83/365; 83/932; 356/237; 358/101;
358/107; 364/474.09; 364/474.13; 382/8
[58] Field of Search ............ 364/468, 474.02, 474.09,
364/474.13, 474.15, 567, 571.01, 571.02, 571.04,
571.05, 551.01, 551.02; 83/365, 522.19, 932,
367, 72–75.5, 76.1, 76.2, 76.3, 76.6–76.9, 13;
356/237, 445; 358/101, 106, 107; 382/8

[56] References Cited

U.S. PATENT DOCUMENTS

| | | | |
|---|---|---|---|
| 4,136,504 | 1/1979 | Wyslotsky | 83/365 X |
| 4,226,540 | 10/1980 | Barten et al. | 356/237 X |
| 4,413,279 | 11/1983 | Görl | 356/237 X |
| 4,875,254 | 10/1989 | Rudy et al. | 83/365 X |
| 5,054,345 | 10/1991 | Weber | 83/365 X |

FOREIGN PATENT DOCUMENTS 522534 6/1982 Australia .
2496269 6/1982 France .

OTHER PUBLICATIONS

European Search Report Jul. 1, 1991.

*Primary Examiner*—Joseph Ruggiero
*Attorney, Agent, or Firm*—Sughrue, Mion, Zinn, Macpeak & Seas

[57] ABSTRACT

A slicing machines includes a control system having a camera (6) which views a cut face (5) of a product being sliced. Image data from the camera (6) is processed to determined a parameter characteristic of the cut face (5). The step of processing the image data includes classifying the image data by comparison with an intensity threshold which is varied automatically in accordance with the populations of data in the different classes. A control signal is generated to control the operation of the slicing machine in accordance with the determined parameter.

In a preferred example, the determined parameter depends on the linear density of the cut face and the control signal varies the thickness of the slices in order to produce a slice having a desired weight.

15 Claims, 6 Drawing Sheets

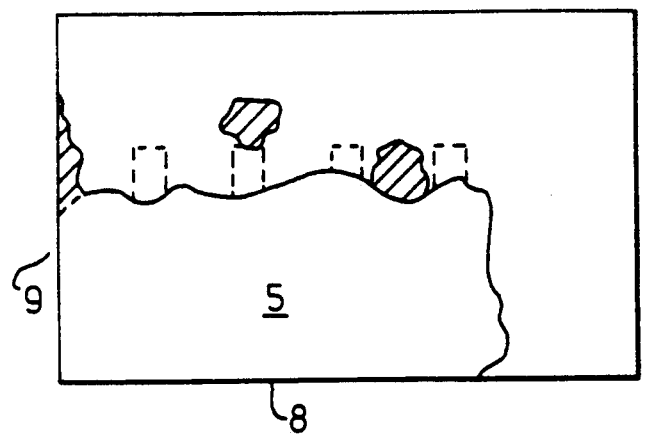
Fig.2(a) E1
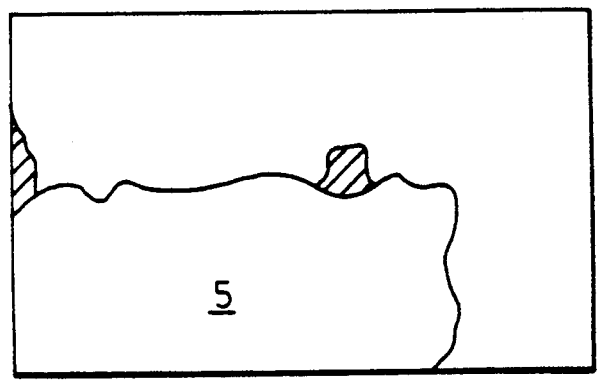
Fig.2(b) E2
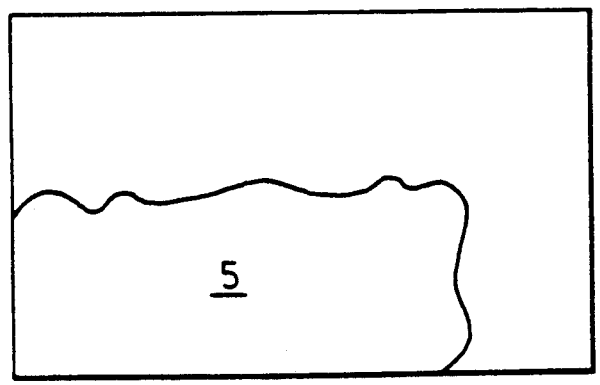
Fig.2(c) E3

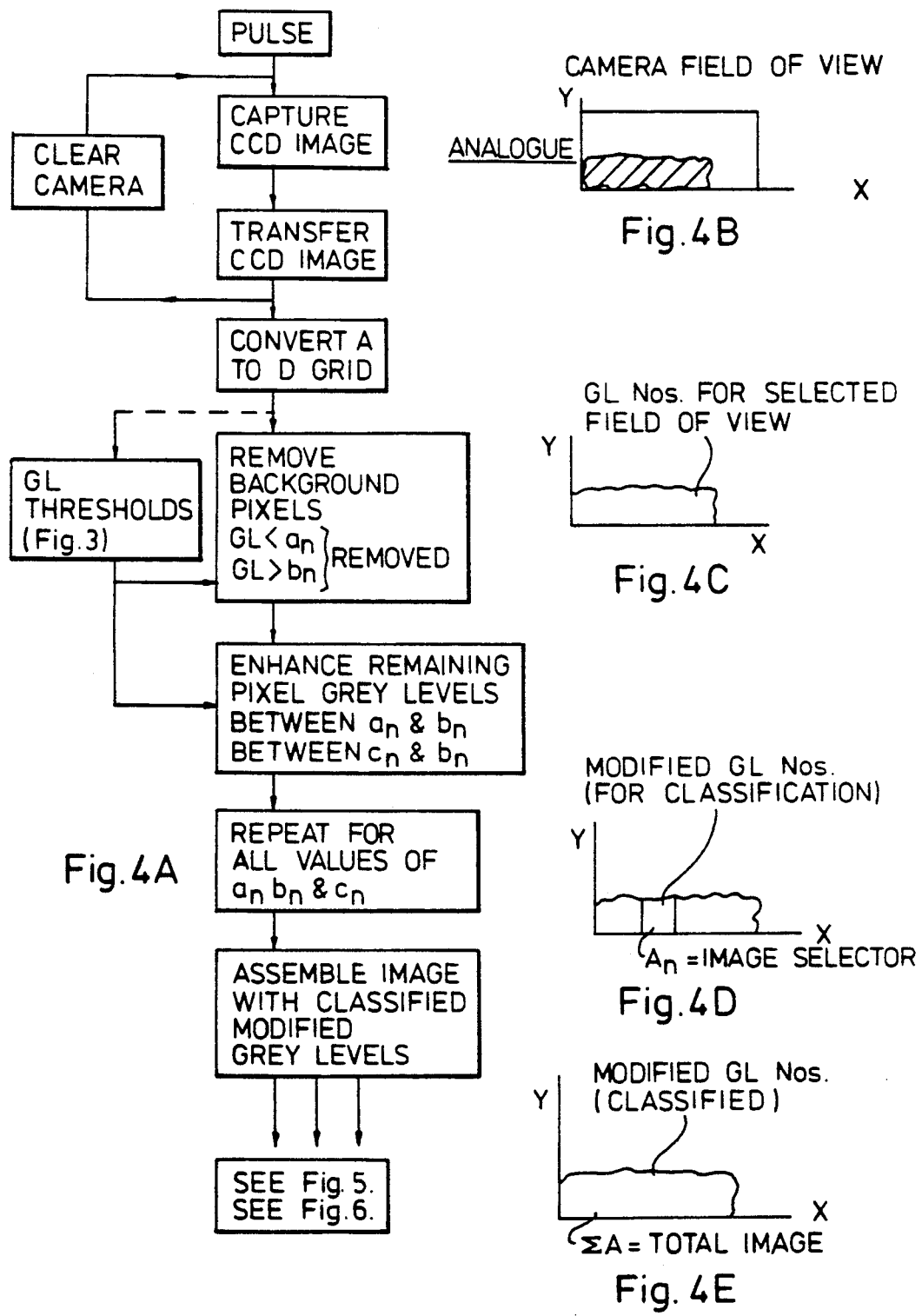

APPARATUS FOR AND METHOD OF CONTROLLING SLICING MACHINE

BACKGROUND TO THE INVENTION

The present invention relates to a slicing machine and a method of control for the machine. Such machines are principally, but not exclusively used for slicing food products, particularly slicing cheese, meat and pressed or moulded meat products.

Typically such a slicing machine includes a rotating blade and means to feed the product forward towards the blade so that successive slices are cut from one face of the product. The distance through which the product is advanced between successive cuts of the blade determines the thickness of the slices. Where the product is of uniform shape and density then it may be sufficient to use a single predetermined slice thickness to give a slice or group of slices of the required weight. In general however variations in the shape and density of the product mean that the weight of a slice of a given thickness varies. A previous approach to dealing with this variation is described and claimed in the applicants' granted European Patent EP-B-0,127,463. This patent describes and claims a process in which an automatic slicing machine is programmed to vary the thickness of the slices in accordance with a typical weight distribution for the product. Although this system achieves good results where the product shape or envelope varies in a predictable manner it still tends to produce a number of slices which are outside the required weight range when the actual weight density distribution departs from the expected distribution.

It has previously been proposed to make some determination of the cross-sectional area of the product as it is cut. This may be done using feelers disposed around the product in the vicinity of the slicing zone, or, for example, by placing a light source and a photodetector array in front of the cut face of the product. The area of the array which is illuminated by the image of the cut face is then used as an indication of the cross-sectional area. Although such a system is better able to cope with variations in the shape of the product it still tends to produce slices which are off-weight when there is variation in density of the product. This is a particular problem when the product is inhomogeneous. For example, bacon comprises both portions of fat and portions of lean and the different proportions of fat to lean vary from slice to slice producing unpredictable variations in the overall slice density.

SUMMARY OF THE INVENTION

According to a first aspect of the present invention, there is provided a method of controlling a slicing machine comprising viewing with a camera, a cut face of a product being sliced; processing image data from the camera to determine a parameter characteristic of the cut face, the step of processing the image data including classifying the image data by comparing the image data with an intensity threshold, and automatically varying the intensity threshold in accordance with the determined populations of data in the different classes; and generating a control signal to control the operation of the slicing machine in accordance with the determined parameter.

The present invention provides a method of control which is not only responsive to overall characteristics of the face of the product, such as its area, but is also able to recognise different classes of data within the face. The different regions are classified according to the intensities of the corresponding pixels in the image data. For example, in bacon, pixels corresponding to areas of fat are seen to have higher intensities than areas of lean which are darker. The analysis of the image data is complicated however by the fact that both the absolute and relative intensities of the different regions of the cut face vary with such factors as the condition of the product, the nature of the source of illumination and the different distances of regions of the face from the source of illumination and the camera. The present invention is able to overcome all these difficulties by automatically re-evaluating the thresholds used in classifying the image data, as described in further detail below.

Different respective thresholds may be provided for different regions of the image data and the different thresholds independently re-calibrated in accordance with the populations of data in the respective regions.

By, for example, analysing selected columns of pixels at regular intervals across the cut face it is possible to normalise the classification process in such a way as to compensate for the reduction in intensity towards the side of the face away from the source of illumination. In some circumstances it is not necessary to calculate a fresh threshold level for each new set of image data. Where there are separate thresholds for different regions at regular intervals across the cut face, the threshold for one region may be updated for one set of image data, the threshold for the adjacent region updated for the next set of image data and so on. In the regions which are not updated the data is classified using the last determined threshold for the region in question.

According to a second aspect of the present invention, there is provided a slicing machine for cutting slices from a product including a camera arranged to view a cut face of the product being sliced; image processing means for processing image data from the camera to determine a parameter characteristic of the cut face, the image processing means including means to classify the image data by comparing it with an intensity threshold, and means to vary the intensity threshold automatically in accordance with the determined populations of data in the different classes; and control signal generating means arranged to generate a control signal to control the operation of the slicing machine in accordance with the determined parameter.

BRIEF DESCRIPTION OF THE DRAWINGS

A slicing machine in accordance with the present invention will now be described in detail with reference to the accompanying drawings in which:

FIGS. 2a to 2c show the field view of the camera of FIG. 1;

FIGS. 4a to 4e are a flow-diagram and graphs showing the use of the grey level thresholds in analysing image data.

DESCRIPTION OF A PREFERRED EXAMPLE

Figure 1:
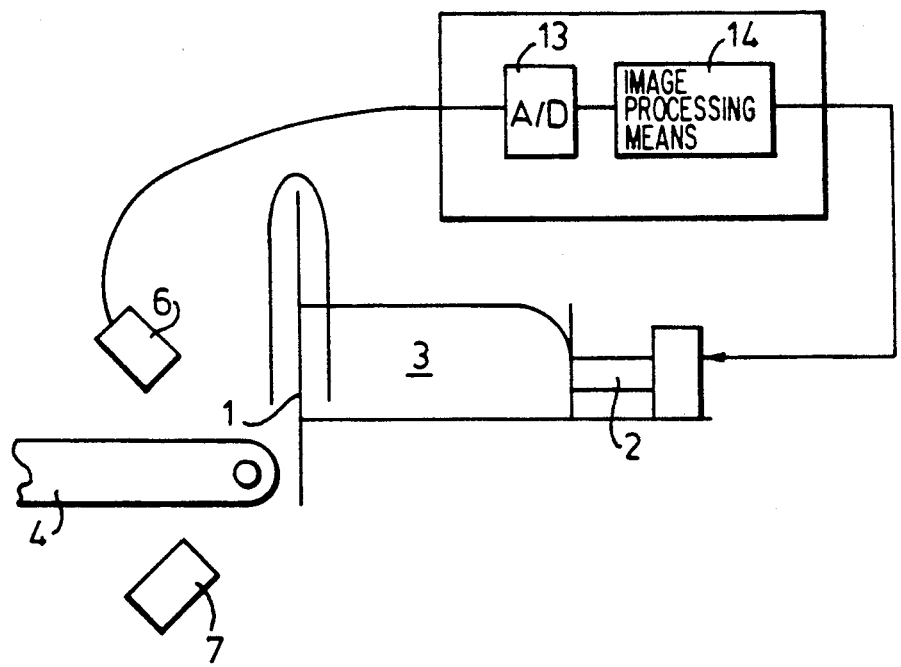
FIG. 1 is a side elevation of the system.

A slicing machine includes a slicing blade 1 and a feed mechanism 2 arranged to advance a product 3 towards the blade 1. Slices cut from the end-face 5 of the product 3 fall onto a conveyor 4. A source of illumination 7 is provided to one side of the end-face 5 of the product 3. The output from a camera 6 is taken to image processing hardware which operates as described in further detail below to generate an appropriate control parameter for the slicer.

The camera 6 is set so that the lower edge of the field of view coincides with the bed shear-edge 8, so that when the product is held against a vertical shear-edge guide 9 the view of the camera encompasses the product on two sides at right-angles to each other. The product is illuminated from below, so that the area within the frame but beyond the product periphery appears much darker than the product face, irrespective of the strength of the illumination source. The camera scan is initiated from a pulse from the slicer blade at the point where the field of view is clear of the blade. The camera 6 may be of any known type with or without distinguishing colour facilities, but will preferably use an asynchronous CCD to ensure rapid capture of the frame.

Using an A/D converter 13 and conventional frame grabbing techniques the output from the camera 6 is converted into an array of pixels for processing by the image processing hardware 14.

The image processing technique may subdivide the image field into any number of comprising areas and determine the optimum boundary thresholds for each so that disturbing effects which occur over the image field, for example asymmetric shading, skew between the axes of illumination and vision, the effects of the temperature gradients over the face of the product, may be compensated. The techniques also permit slice or portion quality segregation based upon the assessment of workface area or shape, or component proportion or its disposition.

The system of the present invention has greatly improved the correlation between the visually apparent density and the actual density of the product and, together with fast processing, has enabled visual observation to be used to control slice and/or portion weight at high speed with more consistency than was hitherto possible.

The basic concept will now be explained using bacon as a product example. This generally contains a proportion of lean and fat which are not uniformly light or dark but can be readily distinguished by the eye under a wide range of lighting conditions. In such a natural product there will be variability in the average density of its lean and fat but the accuracy of slicer control is primarily determined by the accuracy of the area measurements of lean and fat and, consequently, the visual discrimination between them.

The scanning technique employed divides the image field into say, 500 by 500 picture elements or pixels each recording a grey level value in the range of, say, 0 to 250. By selectively sampling an area which contains only bacon a range of pixel grey levels will be observed which, if the bacon contains both fat and lean, will be represented by higher and lower value populations of grey levels.

Although the grey level values will all change in common proportion with any variation in illumination, the ratio between the maximum and minimum grey levels of the two component populations should be substantially constant. In practice the sample may contain extraneous high or low grey level values which may be excluded from any further analysis by excluding preset numbers or fractions of the total pixels in the sample at one or both ends of the grey level value spectrum.

If the grey level ratio of this modified sample, as represented by the ratio of the maximum and minimum grey levels means of the two modified populations, falls within preset limits generally representative of fat and lean in bacon, the threshold grey level distinguishing between fat and lean may be computed for the area of bacon represented by the sample.

This intermediate fat/lean grey level threshold value, being evaluated in part as some preset fraction within the numeric interval between the modified maximum/minimum grey levels may, together with other grey level threshold values within the image field, be conveniently stored in tabular form in a computer memory. Further, a lean/background threshold value may also be evaluated in part as some preset ratio of the lean grey level. The threshold values may be re-evaluated from time to time. Under normal conditions the threshold values vary only gradually with time and between adjacent areas of the image field and so temporal and spatial digital filtering may be used to smooth the stored values or to identify the onset of abnormal conditions, for example, the major contamination of an optical aperture.

In normal operation the advancing face of the product is scanned when the blade and the last severed slice have just cleared and the camera has a free view of the workface. The captured image is transferred to a frame store in computer memory for analysis. By the separate summation of all, or an acceptable representative fraction of all, of the pixels whose grey level is within the appropriate area threshold values, the areas of lean and fat may be calculated.

The total areas of lean and fat so measured may be used not only for the control of slice and/or portion weight but also for the purpose of slice quality classification. Where the ratio of fat to lean of an individual slice or the average ratio of a portion of slices exceeds some preset limit or limits the slice or portion may be diverted to one or more separately classified lines.

For certain classification purposes the fat to lean ratio for only a specified zone or zones within the slice is required. For example, when bacon slices exhibit a substantially continuous wide strip of fat along one edge, a shingle pack may display more fat than lean than is desirable in the market. The calculation of fat to lean ratio may then be confined to a predefined group of pixels in the frame store corresponding to a selected zone of the workface.

In practice, the camera views the advancing face of the product about to be sliced and the image frame is adjusted to just exclude the bottom and the side shear-edges.

The face of the product is illuminated asymmetrically from below, so that the area of the advancing product face is fully illuminated and the area above the product boundary receives no direct illumination and generally appears almost black, as viewed by the camera.

However, scraps of product arising from the product infeed and the slicing operation cannot be avoided and can therefore become illuminated. These may then be seen by the camera and have to be eliminated from any area calculations.

Some of these scraps will be flung out by the blade and deflected by the air-swirl created by the blade motion, so that a progressive build-up of scrap product is unavoidable, from which not even the light emitter or camera can be totally protected.

Consequently, the image perceived will change over a period of time and any optical relationship which may have been used to distinguish between product components in terms of colour or grey levels for product density computations would tend to be invalidated.

In the present invention, to compensate for general visual degradation the parameters according to which each pixel may be classified, for instance as lean or fat, are automatically adjusted.

Since both the camera and the light source are asymmetrically disposed with respect to the advancing face of the product, there will also be differences in the apparent illumination across the whole product surface and these may be further affected by any uneven scrap-dust film on the optical equipment, that is the light emitter window or the camera aperture.

The visual parameters are regularly reviewed and refreshed in rotation for all component areas of the virtual image of the advancing product face by sampling each component area at intervals during the continuous slicing process and interpreting each sample in turn to maintain a valid relationship between the visual thresholds of the product components to enable appropriate density classifications, in spite of apparent changes in illumination across the face of the product, however they may occur.

These regularly updated thresholds are then applied to classify all pixels within each product face image, enhanced according to classification, if required for VDU display, each classification is integrated and multiplied by appropriate density factors and thence converted to a product feed sequence as generally described in the above cited patent.

Figure 3A:
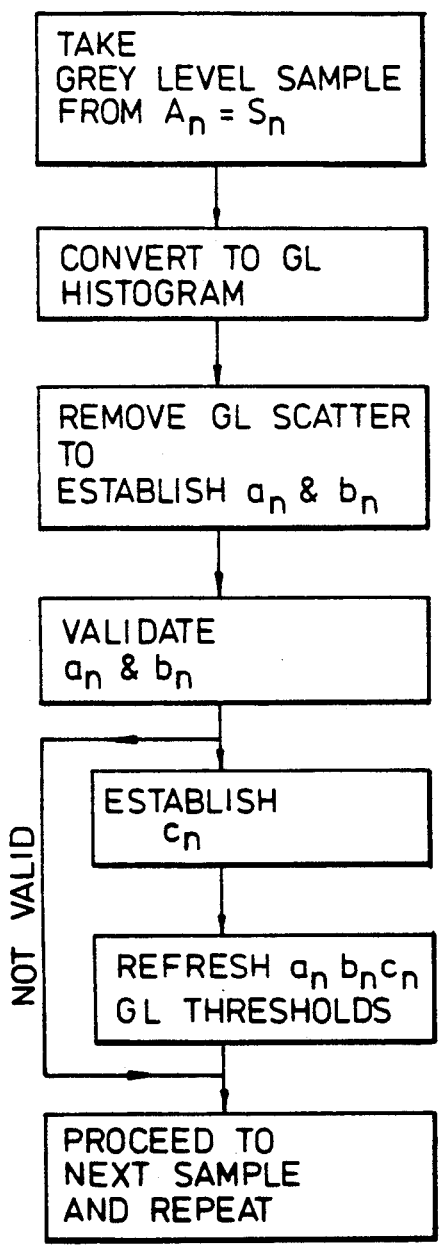
FIGS. 3a to 3c are a flow-diagram and graphs showing the determination of grey level thresholds.
Figure 3B:
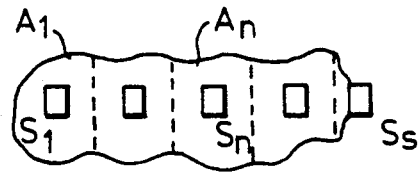
Figure 3C:
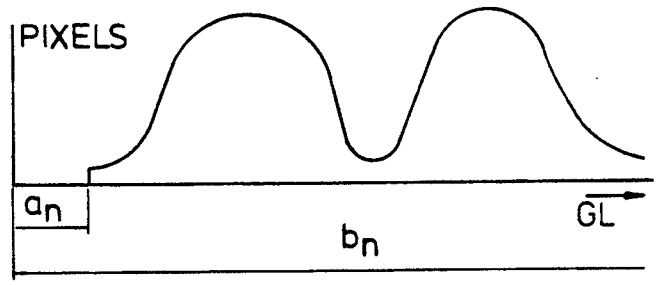

As shown in FIG. 3 sample S(n) is taken in rotation to be representative of meat within area A(n) to compute the Grey Level Thresholds numerically for lean and fat respectively, within zone S(n).

These Grey Level Thresholds are then used to analyse consecutive images of the product face just before a slice is cut and to control the product advance with the object of producing a constant weight slice or portion of slices.

The sample Grey Levels are in a virtual tabular format corresponding to pixel location and the format is then shown modified for illustration purposes to show pixel numbers for each Grey Level as represented by a histogram with elongated tails at each end, indicating scatter.

This scatter is untypical of the bulk of the sample and generally due to minor anomalies (ice crystals, droplets, small voids, etc.) and should, therefore, be removed. The data is treated to establish lower and upper limits a(n), b(n) for the Grey Levels (GL) which exclude the scatter in the tails of the distribution.

Alternative methods to remove scatter may be used.

Preset numbers of pixels are removed from both ends of the Grey Levels to define a(n) and b(n).

Alternatively a(n) and b(n) values are defined by pre-stipulating what the number of pixels at these cut-off points shall be.

Alternatively, gradient values at both ends of the histogram may be stipulated to derive a(n) and b(n).

Validation of these revised Grey Levels is based on the observation that, provided lean and fat are present in the sample, the ratio of Grey Levels between a(n) and b(n) will generally be limited and substantially predictable.

Accordingly the test for validation consists of comparing this ratio with preset maximum and minimum values, which may be operator adjusted to suit the product.

If this criteria is not satisfied, the sample data is dumped, the Grey Level Thresholds are not refreshed and the next sample is taken.

The shape of the histogram in FIG. 3 shows a transition between concentrations of pixels which usually connect across a relatively narrow throat. For all practical purposes, this throat corresponds to neither lean nor fat and the Grey Level value at this point is used to distinguish between lean and fat at c(n) based on a(n) and b(n).

As explained above the image data is periodically sampled, to update the Grey Level thresholds, which may be re-called and used as follows.

As shown in FIG. 4, the digital Grey Level grid is split into Zones which include areas A(1),A(2)–A(n), etc. and each zone is treated separately, preferably in parallel to save time, alternatively sequentially if time allows.

Taking Zone n as an example, for which the latest values of the product threshold Grey Levels are known (See FIG. 3 tabulation of a(n), b(n) and c(n)) all pixels outside a(n) and b(n) are removed, thus retaining only those pixels which represent product.

The remaining product Grey Levels are now contrast enhanced, so that all Grey Levels between a(n) and c(n) and those between c(n) and b(n) convert into fixed and clearly different Grey Levels, for instance Grey Level=100 for fat and Grey Level=200 for lean.

By carrying out identical operations for all the product areas the whole face is numerically enhanced uniformly across its total area, irrespective of the variations in perceived illumination, asymmetric lighting and visual degradation.

For setting up purposes, this fully enhanced pattern is usefully displayed on demand for direct comparison with the camera view, using a VDU, with or without super-imposed numerical data.

Figure 5:
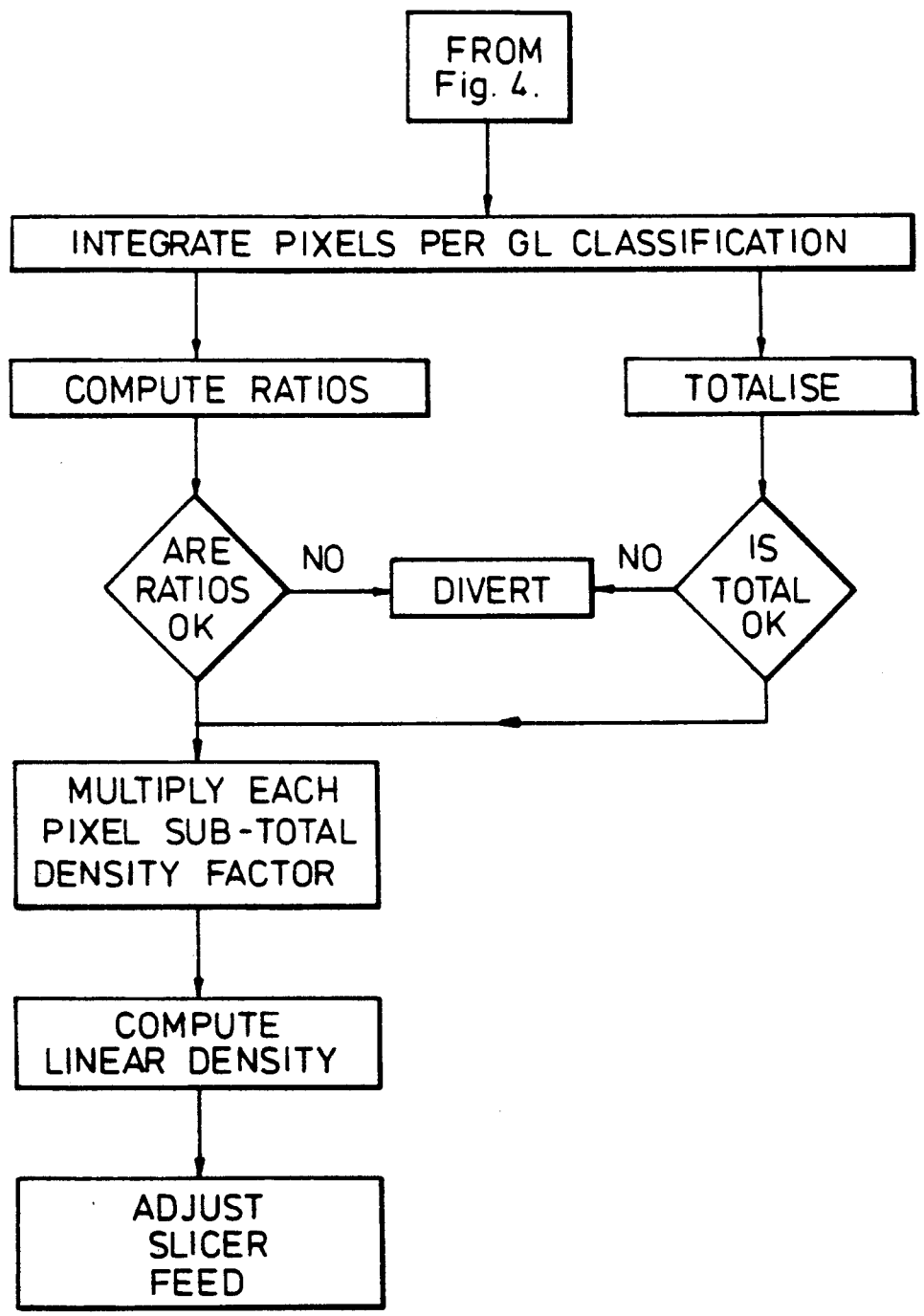
FIGS. 5 and 6 are flow-diagrams.

Further processing of this enhanced data is explained with reference to FIGS. 5 and 6.

This illustrates the route to slicer feed control, subject to:

the lean/fat ratio being acceptable.

the total area of the product face is within predetermined values, so that a commercially unacceptable slice or a portion containing an unacceptable slice may be diverted.

The categorised pixels representing lean and fat are integrated separately and their ratio which represents lean/fat is compared to upper and lower set-points.

The categorised pixels are also totalised and the total number of pixels is also compared to preset upper and lower limits, representative of the largest and smallest permissible slice area.

If either the ratio or the total fall outside predetermined limits, the slice or the portion, complete or partial is diverted.

If both the ratio and the total pixel number are within the preset limits, the pixel sub-totals representing lean and fat are multiplied by their respective density factors to derive the linear density, that is the weight per unit thickness, appropriate to the slice which is about to be sliced.

A standard control loop adjusts the slicer feed to produce a slice of substantially constant weight as described in the above cited patent. The control loop using the camera is found to achieve a consistent 85/95% on-weight performance, compared to a 30 to 60% performance for conventional control systems using a check-weigher rather than a camera.

The distribution of fat and lean in a natural product, such as bacon, can result in portions, particularly shingled portions, which give the appearance of consisting of a large amount of fat and very little lean, because the exposed edges of consecutive slices are substantially fat although the bulk, which is hidden, is mainly lean.

Accordingly, it may be desirable to divert slices or portions which exhibit an excessive amount of fat along one edge.

Figure 6:
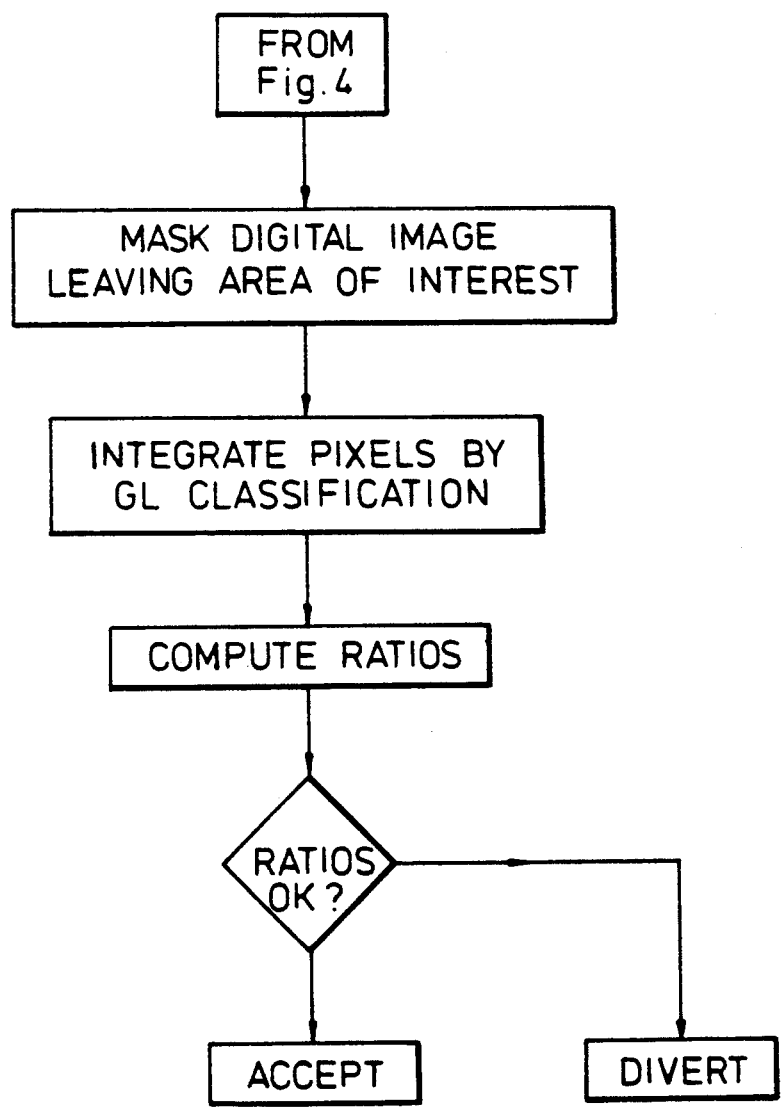

The enhanced digital image from FIG. 4 is effectively masked to leave the appropriate edge area of the slice for computational purposes which, using the thresholds from FIG. 3, computes the lean/fat ratio for the edge area, as explained in FIG. 6 and compares it to a preset limit.

If it falls below a commercially acceptable level, the slice or the portion is diverted.

Further image processing may be used to eliminate image data corresponding to fragments of meat or islands connected to the cut face by narrow necks. The inclusion of such errors can result in miscalculations of the slice weight. The method used to eliminate the features is described in detail in our co-pending application also entitled "Slicing Machine" agents reference 80/3493/04, claiming priority from British application number 9006803.2.

As described above, slices may be rejected because, for example, the total ratio of fat to lean is unacceptably high. However the final acceptability or otherwise of a slice also depends on a number of complex and interrelated characteristics such as the shape of the slice, the distribution of fat within the slice the size of the largest areas of fat within the slice etc. By applying a further stage of discrimination using a neural network, the preferred embodiment of the present invention is able to recognise slices which do not have the desired combination of characteristics, and so further improves the quality and consistency of the product output from the slicing machine.

The neural network itself may be of conventional design and may be implemented in software in an appropriate microprocessor, or alternatively may use dedicated parallel-processing hardware. The network comprises an array of interconnected cells which are trained to fire in response to appropriate input stimuli. Neural network technology is discussed, and various commercial suppliers of both software and hardware-implemented systems identified in the review article "Neural Networks" published at pages 214-245 of Byte, vol. 14, number 8 August 1989, published by McGraw-Hill Inc.

In the present embodiment, the system is first used in a training phase in which slices are cut individually from the product. Each slice is viewed by an assessor, preferably using the contrast-enhanced image from the VDU. The assessor inputs a signal to the system to indicate whether each slice is acceptable. After an appropriate number of slices has been viewed the network is then able to discriminate subsequent slices on the basis of the internal criteria developed during the training phase.

We claim:

1. A method of controlling a slicing machine, comprising:
   viewing with a camera a cut face of a product being sliced;
   processing image data from said camera, thereby determining a parameter characteristic of said cut face; and
   generating and outputting in response to said parameter a control signal for controlling operation of said slicing machine;
   said step of processing said image data including comparing image data with an intensity threshold, thereby determining populations of data in different classes, and automatically varying said intensity threshold in accordance with a distribution of said image data so that said intensity threshold corresponds to a local minimum between said populations having been determined, said parameter characteristic of said cut face being weighted in proportion to said populations of data in different classes.

2. The method of claim wherein said parameter characteristic of said cut face determined by processing the image data is a function of linear density of said cut face, and said control signal varies thickness of slices cut by said slicing machine dependent upon said density of said cut face thereby producing a desired slice weight.

3. The method of claim 1, wherein different respective thresholds are provided for different respective regions of image data, and said different thresholds are independently updated in accordance with populations of data in said respective regions.

4. The method of claim 3, wherein only some of said different respective thresholds are updated in response to each complete set of image data.

5. The method of claim 4, wherein said different thresholds correspond to regions spaced across the image, and a threshold for one region is updated in response to one set of image data and a threshold for a next adjacent region is updated for a next following set of image data.

6. A method of controlling a slicing machine, comprising:
   viewing with a camera a cut face of a product being sliced;
   processing image data from said camera, thereby determining a parameter characteristic of said cut face; and
   generating and outputting in response to said parameter characteristic a control signal for controlling operation of said slicing machine;
   said step of processing said image data including comparing image data with an intensity threshold, thereby determining populations of data in different classes, and automatically varying said intensity threshold in accordance with a distribution of said image data so that said intensity threshold corresponds to a local minimum between said populations having been determined and said parameter characteristic of said cut face being weighted in proportion to said populations of data in different classes, said parameter characteristic being a function of linear density of said cut face and said slicing machine in response to said control signal varying thickness of slices cut by slicing machine in dependence upon said parameter characteristic, thereby producing a desired slice weight.

7. The method of claim 6, wherein different respective thresholds are provided for image data corresponding to different respective regions of said cut face, said thresholds being varied independently in dependence upon populations of data in said respective regions.

8. A control system for a slicing machine for cutting slices from a product, said control system including:
   means for viewing a cut face of a product being sliced and for outputting image data;
   means, coupled to said means for viewing, for processing said image data and thereby determining a parameter characteristic of said cut face; and
   means responsive to said image processing means for generating and outputting a signal to control operation of said slicing machine in accordance with said determined parameter characteristic;
   said means for processing including means for comparing image data with an intensity threshold, thereby determining populations of data in different respective classes, and means for varying automatically said threshold in dependence upon a distribution of said image data so that said intensity threshold corresponds to a local minimum between said populations having been determined.

9. The system of claim 8 wherein said means for processing said image data is arranged to determine from image data a parameter which is a function of linear density of said cut face of said product, and said means responsive to said image processing means being arranged to generate a control signal for controlling a slicing machine to vary a slice thickness in accordance with the density of the cut face thereby producing a desired slice weight.

10. The system of claim 8, wherein said means for processing includes means for calculating different respective thresholds for different regions of image data and means for re-calibrating different respective thresholds independently in accordance with populations of data in said respective regions.

11. The system of claim 10, wherein said means for recalibrating different thresholds is arranged to update only some of said different thresholds in response to each complete set of image data.

12. The system of claim wherein said different thresholds correspond to regions spaced across said image, and said means for re-calibrating is arranged to update a threshold for one region in response to one set of image data, and to update a threshold for a next adjacent region in response to a next set of image data.

13. A slicing machine for cutting slices from a product, comprising:
   a slicing blade;
   means for advancing a product towards said slicing blade; and
   means, coupled to said means for advancing, for controlling a distance by which said product is advanced between successive slices, thereby determining the slice thickness;
   wherein said means for controlling comprises:
   means for viewing a cut face of a product being sliced and for outputting image data;
   means, coupled to said means for viewing, for processing said image data and thereby determining a parameter characteristic of said cut face; and
   means responsive to said image processing means for generating and outputting a signal to control operation of said slicing machine in accordance with said parameter characteristic having been determined;
   said means for processing including means for comparing image data with an intensity threshold, thereby determining populations of data in different respective classes, and means for varying automatically said threshold in dependence upon a distribution of said image data so that said intensity threshold corresponds to a local minimum between said populations having been determined.

14. A method of controlling a slicing machine, comprising:
   viewing with a camera a cut face of a product being sliced;
   processing image data from said camera, thereby determining a parameter characteristic of said cut face; and
   generating and outputting in response to said parameter characteristic a control signal for controlling operation of said slicing machine;
   said step of processing said image data including comparing image data with an intensity threshold, thereby determining populations of data indifferent classes, and automatically varying said intensity threshold in accordance with a distribution of said image data, thereby locating said intensity threshold in the region of a local minimum between said populations having been determined,
   said parameter characteristic of said cut face being weighted in proportion to said populations of data indifferent classes,
   said step of processing said image data further comprising making separate, independent determinations of said intensity threshold for different respective regions of said image data.

15. The method of claim 14, wherein said different thresholds correspond to regions spaced across the image, and a threshold for a first region is updated in response to a first set of image data and a threshold for a second adjacent region is updated for a second following set of image data.

* * * * *